United States Patent [19]
Chao et al.

[11] Patent Number: 5,059,737
[45] Date of Patent: Oct. 22, 1991

[54] CATALYTIC CONDENSATION PROCESS

[75] Inventors: Tai-Hsiang Chao, Mt. Prospect; Fiona P. Wilcher, Wilmette; Mark R. Ford, Buffalo Grove; Andrzej Z. Ringwelski, Marengo, all of Ill.

[73] Assignee: UOP, Des Plaines, Ill.

[21] Appl. No.: 546,971

[22] Filed: Jul. 2, 1990

Related U.S. Application Data

[63] Continuation-in-part of Ser. No. 288,921, Dec. 23, 1988, Pat. No. 4,946,815.

[51] Int. Cl.$^5$ ............... C07C 2/66; C07C 2/18; C07C 1/20; B01J 21/16
[52] U.S. Cl. .................. 585/466; 568/898; 585/469; 585/529; 585/639; 585/640
[58] Field of Search ........... 585/466, 469, 529, 639, 585/640; 568/898

[56] References Cited

U.S. PATENT DOCUMENTS

| | | | |
|---|---|---|---|
| 2,116,151 | 5/1938 | Ipatieff et al. | 502/214 |
| 2,275,182 | 3/1942 | Ipatieff et al. | 502/214 |
| 2,650,201 | 8/1953 | Mavity | 252/435 |
| 2,960,477 | 11/1960 | Smith et al. | 252/43 |
| 3,050,472 | 8/1962 | Morrell | 502/214 |
| 3,112,350 | 11/1963 | Bielawski et al. | 260/683.15 |
| 3,661,801 | 5/1972 | Gutmann et al. | 252/435 |
| 3,673,111 | 6/1972 | Hovarth et al. | 252/435 |
| 3,801,704 | 4/1974 | Kobayashi et al. | 423/309 |
| 4,521,638 | 6/1985 | Kida et al. | 585/640 |
| 4,946,815 | 8/1990 | Chao et al. | 252/81 |

FOREIGN PATENT DOCUMENTS 1096891 1/1961 Fed. Rep. of Germany ...... 502/214

*Primary Examiner*—Asok Pal
*Attorney, Agent, or Firm*—Thomas K. McBride; John F. Spears, Jr.

[57] ABSTRACT

A hydrocarbon conversion process which utilizes a solid phosphoric acid catalyst having a total X-ray intensity of at least 40 percent relative to alpha-alumina. The solid phosphoric acid catalyst is produced by crystallizing an amorphous mixture of an acid oxide of phosphorus and a siliceous material at a temperature of from 350° to 450° C. and in the presence of from 10 to 50 mole percent water vapor based upon the total vapor rate to the crystallizing means. Embodiments of the new hydrocarbon conversion process include alkylation, oligomerization, and hydration, of hydrocarbons and oxygenated hydrocarbons.

11 Claims, 1 Drawing Sheet

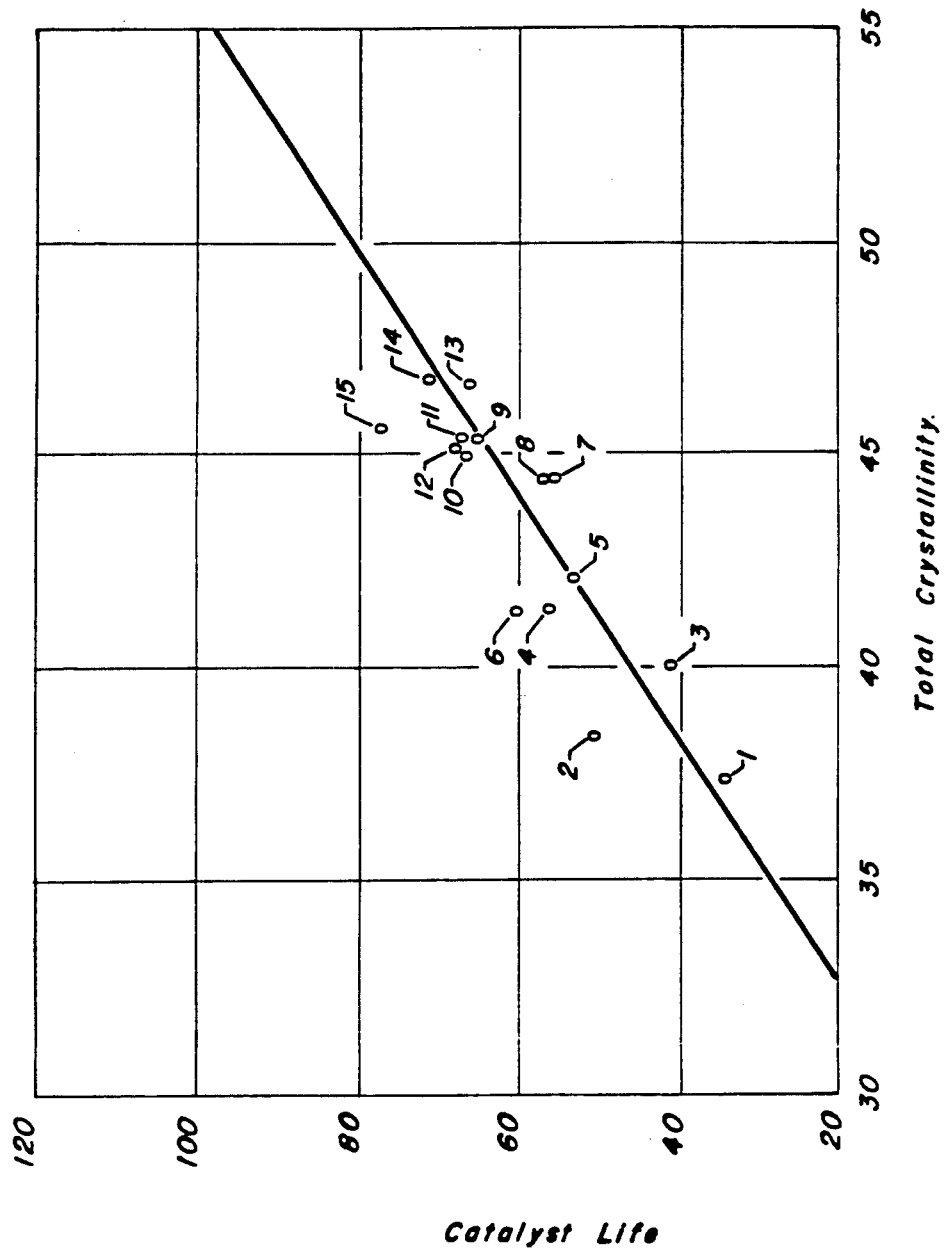

CATALYTIC CONDENSATION PROCESS

CROSS-REFERENCE TO RELATED APPLICATION

This application is a continuation-in-part of co-pending application Ser. No. 288,921 which was filed Dec. 23, 1988 and subsequently allowed, now U.S. Pat. No. 4,946,815 issued Aug. 7, 1990.

BACKGROUND OF THE INVENTION

This invention relates to an improved hydrocarbon conversion process which utilizes a solid phosphoric acid catalyst composition having a total silicon phosphate X-ray intensity greater than 40.0 percent relative to alpha-alumina and having been prepared by specific calcination conditions. In particular embodiments, the hydrocarbon conversion process comprises alkylation, oligomerization, hydration, and etherification of hydrocarbons and oxygenated hydrocarbons. Well-known products of said particular embodiments are high-octane gasoline, alcohols, and speciality chemicals such as xylene and cumene.

Solid phosphoric acid catalyst is especially well known for its usefulness in the hydrocarbon conversion processes of aromatic alkylation and olefin polymerization. The catalyst is composed of a support or substrate portion onto which is incorporated an acid fraction for catalytic activity. It is believed that the substrate portion is formed from the silica-phosphoric acid reaction, principally silicon orthophosphate, $Si_3(PO_4)_4$, silicon pyrophosphate, $SiP_2O_7$, as well as derivatives of these compounds. The catalyst is typically prepared by mixing silica with phosphoric acid followed by extrusion and calcination. The reactions are simply illustrated as follows:

$$3SiO_2 + 4H_3PO_4 \rightarrow Si_3(PO_4)_4 + 6H_2O$$

$$SiO_2 + 2H_3PO_4 \rightarrow SiP_2O_7 + 3H_2O$$

The above reactions indicate that the phosphoric acid will react with silica to yield both types of phosphates depending upon stoichiometry and reaction conditions. The silicon orthophosphate can also be dehydrated during drying to give the silicon pyrophosphate, and this is believed to be the alternate mechanism for the silicon pyrophosphate formation. The silicon ortho- to pyrophosphate conversion also depends on factors such as temperature and hydration, as illustrated by the following equations:

$$Si_3(PO_4)_4 + 2H_3PO_4 \rightarrow 3SiP_2O_7 + 3H_2O$$

$$Si_3(PO_4)_4 + heat \rightarrow 2SiP_2O_7 + SiO_2$$

These reactions have made the catalyst manufacturing more complex. Low activity or low stability catalysts have resulted due to low crystallinity caused by poor crystallization conditions.

DESCRIPTION OF THE PRIOR ART

Hydrocarbon conversion processes which utilize solid phosphoric acid catalysts and methods of optimizing physical properties such as crush strength of such catalysts are well known in the art. However, an improved hydrocarbon conversion process which exploits solid phosphoric acid catalyst which possesses greater reaction stability due to increased total silicon phosphate crystallinity is heretofore unknown.

U.S. Pat. No. 2,650,201 to J. Mavity describes a process for improving the structural strength of a calcined solid phosphoric acid catalyst by adding a hydrolyzable compound of a metal selected from a group consisting of titanium, zirconium, and tin to the composite prior to calcination of the metal containing solid phosphoric acid catalyst. The desirable calcination temperature ranges from 100° to 500° C. In distinction, the catalyst of the instant invention does not comprise any added metal component nor does the '201 disclosure mention the benefit obtained by maximizing the silicon phosphate crystallinity.

U.S. Pat. No. 3,112,350 to M. Bielawski et al. discloses a process for the polymerization of hydrocarbon olefins in the presence of a specific solid phosphoric acid catalyst. This specific catalyst comprises a specific high $P_2O_5$ to $SiO_2$ mole ratio in excess of about 1.08. The catalyst is also required to be a calcined at a temperature of preferably above 560° C. The '350 disclosure teaches of the advantages of calcining the catalyst at above 560° C. to achieve a specific crystallite ratio of crystalline form C to crystalline form B of about 28:1. However, when the $P_2O_5$ to $SiO_2$ mole ratio exceeds 1.08 as specified by the prior art, only materials with phosphate content higher than silicon pyrophosphate ($SiP_2O_7$, $P_2O_5/SiO_2 = 1$) are likely to be present. Silicon orthophosphate ($Si_3(PO_4)_4$) is not likely to be present since it only has the $P_2O_5/SiO_2$ ratio of 0.75. Although the '350 disclosure discusses catalyst crystallinity ratio as a basis for optimizing the performance, no mention on the total crystallinity amount requirement was observed.

U.S. Pat. No. 3,673,111 to E. Hovarth et al. discloses a process for the manufacture of a solid phosphoric acid catalyst by two-step calcination to improve the catalyst physical strength. Higher crush strength was obtained when the unfinished catalyst is exposed to steam at temperature of from 260° to 426° C. for a period of time followed by a second calcination in the absolute absence of steam.

U.S. Pat. No. 3,801,704 to M. Kobayashi et al. discloses a solid acidic aluminum phosphate catalyst. It has little relevance to the instant invention where a high stability solid phosphoric acid catalyst with only silicon phosphate crystalline phases are detected by X-ray.

U.S. Pat. No. 4,521,638 to Kida et al. discloses a process for preparing tertiary olefins employing a solid phosphoric acid catalyst. The useful catalyst of the process is calcined at a temperature of greater than 500° C., preferably above 600° C., especially preferably above 700° C. in an inert atmosphere. If the calcination temperature is lower than 500° C., a catalyst having a sufficient activity and a long life cannot be obtained (column 4, line 63 to column 5, line 2). This differs from that of the instant invention in which the high stability solid phosphoric acid catalyst was obtained by improving the total silicon phosphates crystalline content in part by calcining at temperatures lower than about 450° C.

U.S. Pat. No. 2,116,151 to Ipatieff et. al. discloses a method of manufacturing solid phosphoric acid wherein catalyst is calcined in a dry atmosphere at a temperature less than 600° F.

U.S. Pat. No. 2,275,182 to Ipatieff et. al. discloses a method of manufacturing solid phosphoric acid catalyst wherein catalyst is calcined in a dry atmosphere at a temperature of from 600° to 950° F. and then rehydrated by contact with steam in the approximate range of 400°-600° F.

U.S. Pat. No. 3,661,801 to Gutmann et. al. discloses a method of manufacturing solid phosphoric acid catalyst wherein catalyst is calcined in dry air and then rehydrated by contact with steam and air.

U.S. Pat. No. 2,960,477 to Smith et. al. discloses a method of manufacturing solid phosphoric acid catalyst wherein siliceous support is impregnated with phosphorous by soaking the support material in an aqueous solution of phosphoric acid.

U.S. Pat. No. 3,050,472 to Morrell discloses a solid phosphoric acid catalyst comprising phosphoric acid, porous silica material, and mineral talc.

OBJECTS AND EMBODIMENTS

It has been discovered that improved catalyst stability in hydrocarbon conversion reactions is achieved by maximizing the total crystalline content and optimizing the crystallinity phase distribution in a solid phosphoric acid catalyst. Furthermore, this higher silicon phosphate crystallinity product is obtained in a controlled manner by closely controlling steam levels, times, and temperatures during the crystallization step. The instant invention is a new hydrocarbon conversion process which utilizes this improved catalyst to convert hydrocarbon and oxygenated hydrocarbon feedstocks. The new process exploits enhanced catalyst life which the improved catalyst exhibits due to increased catalyst crystallinity and improved crystallinity phase distribution.

Accordingly, a broad embodiment of the present invention is a process for conversion of hydrocarbons or oxygenated hydrocarbons by contacting at hydrocarbon conversion conditions, a hydrocarbon or oxygenated hydrocarbon feedstock with a solid phosphoric acid catalyst. The solid phosphoric acid catalyst is characterized in that it has a total silicon phosphate X-ray intensity greater than 40 percent relative to alpha-alumina. The solid phosphoric acid catalyst is further characterized in that it includes crystallites of both silicon orthophosphate and silicon pyrophosphate but need not be limited to these crystalline phases. The desired crystallinity is produced by crystallizing an amorphous mixture of an acid oxide of phosphorus and a siliceous material at controlled conditions. The crystallizing of the catalyst is ideally conducted in a crystallizing means containing one or more crystallizing zones at a temperature of from 350° to 450° C. and a steam level of from 10 to 50 mole percent based upon the total vapor in the crystallizing zone.

In a narrower embodiment, the instant solid phosphoric acid catalyst is characterized in that it has a total silicon phosphate X-ray intensity greater than 40 percent relative to alpha-alumina by integrating the (002) peak silicon pyrophosphate and (113) peak of silicon orthophosphate and dividing the raw integrated intensities of silicon phosphate phases by the sum of raw integrated intensities of (012), (104), and (113) peaks of an alpha-alumina external standard. The solid phosphoric acid catalyst comprises silicon pyrophosphate crystallites with at least 0.1 X-ray intensity and silicon orthophosphate crystallites with at least 30.0 percent X-ray intensity, both relative to alpha-alumina. The desired phosphoric acid crystallinity can be produced by crystallizing an amorphous mixture of an acid oxide of phosphorus and a siliceous material in a crystallizing means containing one or more crystallizing zones at a temperature of from 350° to 450° C., at a steam level of from 10 to 25 mole percent based upon the total vapor level in the crystallizing zone of zones for a total period of time ranging from 20 to 120 minutes.

DESCRIPTION OF THE DRAWING

The FIGURE is a graphical representation of the catalyst life properties in gallons of hydrocarbon processed per pound of solid phosphoric acid catalyst in relation to total crystallinity of the catalyst. The propylene condensation reaction was used for obtaining this catalyst life data.

DETAILED DESCRIPTION OF THE INVENTION

Solid phosphoric acid catalysts are well known for their utility in various important hydrocarbon conversion processes. However, there have always been problems associated with the use of solid phosphoric acid catalyst in such processes including catalyst activity, catalyst dissolution, catalyst strength, catalyst life, and the like. Therefore, ways to produce active, strong catalysts are always being pursued. To approach this goal, a long life catalyst formulation has been invented by way of catalyst crystallinity optimization. The instant invention is a new process which utilizes the long life catalyst.

The essential and active ingredient of the solid catalyst herein contemplated is an acid of phosphorus, preferably one in which the phosphorus has a valence of +5. The acid may constitute from about 60 to about 80 wt. % or more of the catalyst mixture ultimately produced, and is preferred to be over 80 wt. % thereof. Of the various acids of phosphorus, orthophosphoric acid ($H_3PO_4$) and pyrophosphoric acid ($H_4P_2O_7$) find general application in the primary mixture, due mainly to their cheapness and to the readiness with which they may be procured, although this invention is not restricted to their use but may employ any of the other acids of phosphorus insofar as they are adaptable. It is not intended to infer, however, that the different acids of phosphorus, which may be employed will produce catalysts which have identical affects upon any given organic reactions as each of the catalysts produced from different acids and by slightly varied procedure will exert its own characteristic action. However, it is believed that the catalyst produced having the crystallizing properties disclosed herein will have superior hydrocarbon conversion properties in comparison to catalysts using similar precursors but different manufacturing methods.

In using orthophosphoric acid as a primary ingredient, different concentrations of the aqueous solution may be employed from approximately 75 to 100 percent or acid containing some free phosphorus pentoxide may even be used. By this is meant that the ortho acid may contain a definite percentage of the pyro acid corresponding to the primary phase of dehydration of the orthophosphoric acid. Within these concentration ranges, the acids will be liquids of varying viscosities and will readily mix with adsorbent materials. In practice, it has been found that pyrophosphoric acid corresponding to the formula $H_4P_2O_7$ can be incorporated with siliceous materials at temperatures somewhat above its melting point (61° C.) and that the period of heating which is given to the pyro acid adsorbent mixtures may be different from that used when the ortho acid is so employed.

Triphosphoric acid which may be represented by the formula $H_5P_3O_{10}$ may also be used as a starting material for preparation of the catalyst of this invention. These catalytic compositions may also be prepared from the siliceous materials mentioned herein and phosphoric acid mixtures containing orthophosphoric, pyrophosphoric, triphosphoric, and other polyphosphoric acids.

The material which may be employed as adsorbents or carriers for oxygen acids of phosphorus are divided roughly into two classes. The first comprises materials of predominantly siliceous character and includes diatomaceous earth, kieselguhr, and artificially prepared porous silica. The second class of materials which may be employed either alone or in conjunction with the first class comprises generally certain members of the class of alumina silicates and includes such naturally occurring substances as various fullers earth and clays such as bentonite, montmorillonite, acid treated clays, and the like. Each adsorbent or supporting material which may be used will exert its own specific influence upon the net effectiveness of the catalyst composite which will not necessarily be identical with that of other members of the class.

In producing the catalyst composites which are utilized in the present invention, an oxygen acid of phosphorus and a solid silaceous material are mixed at a temperature of from about 10° to about 232° C. and preferably at a temperature of from about 95° to about 180° C. to form a composite. Thus, satisfactory results have been obtained by heating polyphosphoric acid (82% $P_2O_5$ content) at a temperature of about 170° C. and then mixing this hot acid with diatomaceous earth. The polyphosphoric acid and diatomaceous earth form a composite in which the weight ratio of phosphorus pentoxide to diatomaceous adsorbent is from about 1.8 to about 6.0. This composite is slightly moist to almost dry in appearance but becomes plastic when subjected to pressure in a hydraulic press-type or auger-type extruder by which the composite is formed in to pieces that are cut into shaped particles. This amorphous extrudate is then crystallized to produce the final catalyst with desired properties.

The crystallization of the amorphous extrudate may be accomplished in any known crystallizing means known in the art in which temperature, steam rate, and time in the crystallizing apparatus may be controlled. Conditions of temperature, steam addition rate, and time in the crystallization apparatus all directly impact on the final type and amount of crystallites in the finished solid phosphoric acid catalysts. As mentioned, it is preferred that the finished solid phosphoric acid catalyst have a total silicon phosphate X-ray intensity of at least 40 percent relative to an alpha-alumina standard, and comprise crystallites of both silicon orthophosphates and silicon pyrophosphates.

The term "crystallization" means apparatus or process as used in the instant application and refers to any type of apparatus in which one may control temperature, steam rate, and time in the apparatus in order to optimize the desired crystallinity properties of the solid phosphoric acid catalyst of this invention.

Specifically, such crystallizing means will be an oven or furnace. Typical of such apparatuses known in the art are muffle ovens or furnaces, kilns, and batch or continuous calciners. The crystallization can obviously be accomplished in a batch or continuous manner. Such a crystallizing means may contain one or more zones where temperature, time, and steam level can be controlled.

Temperature is the first critical crystallization condition. Temperature is important in both dehydrating the amorphous material and in controlling the type of crystallites produced as a result of the crystallizing procedures. It is well known that high temperatures, especially those above 500° C. result in a solid phosphoric acid catalyst comprising essentially only crystallites of silicon pyrophosphate. As a result of desiring a catalyst with crystallites of both silicon orthophosphate and silicon pyrophosphate, it was determined that crystallization temperatures ranging from 250° to 450° C. were most desirable and especially temperatures between 350° and 450° C.

In conjunction with a specific crystallizing temperature, it is also an important aspect of this invention that the steam, or moisture content of the crystallizing means be controlled closely to result in the desired crystallinity properties of the catalyst. It is desired that the steam content of the vapor of the crystallization zone or zones range from 10 to 50 mole percent based upon the total vapor content of the crystallization zone. It is most preferred that the steam level range from 10 to 25 mole percent on the total vapor rate to the crystallization zone.

It should be noted that controlling the steam content of the crystallization zone vapors does not necessarily mean that all or even part of the steam to the crystallization zone must be added from an outside source. It is quite possible that much of the steam will be present in the vapor in the crystallization zone as a result of evaporation of water from the catalyst during the crystallization. Steam addition to the crystallization zone or zones will likely be required but the variable might also be controlled by controlling such variables as total vapor rate through the crystallization zone or zones, temperature, and green catalyst moisture content among others.

Time in the crystallization process is also important. Typically, the total crystallization time will vary from 20 to 120 minutes. When more than one crystallization zone is used, the total time in each may vary such that the total crystallization time ranges from 20 to 120 minutes.

It is a further preferred aspect of this invention that where there is more than one crystallization zone, at least one crystallization zone must be operated at the conditions above. It is further preferred that the terminal or final crystallization zone in a multiple step crystallization process is operated at the desired process conditions detailed above. Keeping in mind that the desired temperature range will typically be the highest crystallization temperature the catalyst will see, it becomes reasonable to operate the terminal crystallization zone at the temperature and steam conditions that will optimize the catalyst total crystallinity and crystallite type. This is not to say that other crystallization zones besides the terminal zone cannot be operated at the preferred operating conditions. It is believed that this is the most efficient way of producing the catalyst disclosed herein.

A solid phosphoric acid catalyst produced by the method above will have a total silicon phosphate X-ray intensity greater than 40 percent relative to an alpha-alumina standard. The preferred catalyst also will comprise pyrophosphate crystallites with preferably at least 0.1 percent X-ray intensity relative to alpha-alumina.

The crystallinity type and total crystallinity of the finished solid phosphoric acid catalyst is determined by X-ray diffraction using a National Bureau of Standards alpha-alumina reference material. This analysis provides relative values of silicon orthophosphate and silicon pyrophosphate both with respect to alpha-alumina not relative to each other and not absolute values of crystallinity.

To determine the relative crystallinity of a finished solid phosphoric acid catalyst sample, the sample is first ground to fine powder ($-325$ mesh). The sample is then inserted into an X-ray diffractometer equipped with preferably cooper anode X-ray tube and a quantitative diffraction scan is acquired. Raw integrated intensities of silicon phosphate phases are acquired by integrating the (002) peak of silicon pyrophosphate and (113) peak of silicon orthophosphate. Also obtained is the raw integrated intensity of an alpha-alumina external standard by integrating the (012), (104), and (113) peaks. Relative X-ray intensities of silicon phosphate phases are obtained by dividing their respective raw integrated intensities by the sum of raw integrated intensities of three peaks of an alpha-alumina external standard. The result is multiplied by 100 and expressed in percent units.

The X-ray diffraction results reported herein are expressed in values such as total relative crystallinity, silicon orthophosphate crystallinity and silicon pyrophosphate crystallinity, and finally in terms of a relative intensity ratio.

Total relative crystallinity is synonymous to total crystallinity. The total crystallinity of the solid phosphoric acid catalyst in the sum of the silicon orthophosphate crystallinity relative to alpha-alumina, and silicon pyrophosphate crystallinity relative to alpha-alumina. The relative intensity ratio refers to the ratio of the silicon orthophosphate crystallinity relative to alpha-alumina divided by the silicon pyrophosphate crystallinity relative to alpha-alumina.

In a broad embodiment, the instant invention is a hydrocarbon conversion process. Examples of particular hydrocarbon conversion processes are alkylation, oligomerization, and production of alcohol from olefins. Note that the term "hydrocarbon conversion process" is intended to include processes which chemically transform oxygenated hydrocarbons. Alcohols and ethers are examples of oxygenated hydrocarbons. Similarly, the term "hydrocarbon or oxygenated hydrocarbon feedstock" means a charge to a process which comprises hydrocarbons or oxygenated hydrocarbons.

The catalyst of this invention is useful in catalytic condensation, aromatic alkylation, alcohol production from olefins, and other types of hydrocarbon conversion processes. When employed in the conversion of olefinic hydrocarbons into polymers, the catalyst formed as heretofore set forth is preferably employed as a granular layer in a heated reactor which is generally made from steel and through which the preheated hydrocarbon fraction is directed. Thus, the solid catalyst of this process may be employed for treating mixtures of olefin-containing hydrocarbon vapors to effect olefin polymerization, but the same catalyst may also be used at operating conditions suitable for maintaining liquid phase operation during polymerization of olefinic hydrocarbons, such as butylenes, to produce gasoline fractions. When employed in the polymerization of normally gaseous olefins, the formed catalyst particles are generally placed in a vertical, cylindrical treating tower and the olefin-containing gas mixture is passed downwardly therethrough at a temperature of from about 140° to about 290° C. and at a pressure of from about 6.8 to about 102 atmospheres. These conditions are particularly applicable when dealing with olefin-containing material which may contain from approximately 10 to 50 percent or more of propylene and butylenes. When operating on a mixture comprising essentially propylene and butylenes, this catalyst is effective at temperatures from about 140° to 250° C. and at a pressure of from about 34 to about 102 atmospheres.

When employed in the alkylation of aromatic hydrocarbons, the catalyst of this invention may be located in tubular reactors or single, fixed beds of catalyst. Xylenes, cumene, and linear alkyl benzene are examples of useful products which can be formed by the alkylation of aromatic hydrocarbons. Temperatures which are suitable for the alkylation of aromatics with the instant catalyst are those temperatures which initiate a reaction between an aromatic substrate and the particular olefin used to selectively produce the desired monoalkylaromatic compound. Generally, temperatures suitable for use are from about 100° to about 390° C., especially from about 150° to about 275° C. Pressures which are suitable for use herein preferably are above about 1 atmosphere but should not be in excess of about 130 atmospheres. An especially desirable pressure range is from about 10 to about 40 atmospheres with a liquid hourly space velocity (LHSV) based upon the aromatic feed rate of from about 0.1 to about 50 hr$^{-1}$, and especially from about 0.5 to about 5 hr$^{-1}$. It should be noted that the temperature and pressure combination used herein is to be such that the alkylation reaction takes place in essentially the liquid phase. In an essentially liquid phase process for producing alkylaromatics, the catalyst is continuously washed with reactants, thus preventing buildup of coke precursors on the catalyst. This results in reduced amounts of carbon forming on said catalyst in which case, catalyst cycle life is extended as compared to a gas phase alkylation process in which coke formation and catalyst deactivation is a major problem. By "essentially liquid phase" it is meant that all of the active reactants are in the liquid phase, however, there may be inert compounds that exist in the vapor phase such as light paraffins.

When employed in the production of alcohols from olefinic hydrocarbons, the temperature of the solid phosphoric acid bed should be maintained within the range of from about 250° C. to about 350° C., and preferably within the range of from about 265° C. to about 300° C. The catalyst bed temperature should not be allowed to rise above about 350° C., for at temperatures above this limit the over-all efficiency of the process falls off substantially, the conversion of the olefin to the alcohol per pass through the catalyst being reduced, and also a substantial portion of the olefin being either converted into a polymer thereof, or into products of an undesirable nature which, along with the polymer, are difficult to separate from the alcohol and which reduce the over-all yield of alcohol obtainable. If temperatures below about 250° C. are employed, the conversion level again falls off and becomes impractically low.

The total pressure within the reaction system should be at least 34 atmospheres, the maximum pressure being determined primarily by the limitations of the equipment used. It may be desirable in some cases to employ pressures of up to 340 atmospheres but in the usual case pressures within the range of from about 51 to about 85 atmospheres will be found most satisfactory.

The rate at which the feed gases are passed through the catalyst bed is not critical, preferred practice requiring that the GHSV of the system is between about 1200 and about 3000. By the symbol GHSV is meant the "gas hourly space velocity" which is determined in any particular case by dividing the volume of gas fed (cubic feet) per hour (at standard temperature (25° C.) and pressure (760 mm.Hg) by the bulk volume of the catalyst (cubic feet). Water vapor or other condensible gases are considered as non-condensible for calculation of the GHSV of the system.

Further information in the production of alcohols from olefinic hydrocarbons may be obtained by reference to U.S. Pat. No. 2,960,477.

During use of this catalyst in hydrocarbon conversion processes, it is often of value to add small amounts of moisture to prevent excessive dehydration and subsequent decrease in catalyst activity and in order to substantially prevent loss of water from the catalyst. An amount of water or water vapor such as steam is added to the charged hydrocarbon so as to substantially balance the water content of the catalyst. This amount of water vapor varies from about 0.1 to about 6.0 percent by volume of the organic material charged.

The following examples are presented in illustration of the method of this invention and are not intended as an undue limitation on the generally broad scope of the invention as set out in the appended claims.

EXAMPLE 1

This example illustrates the general preparation method for the amorphous form phosphoric acid catalyst extrudate that is converted by various crystallization methods of the subsequent examples into crystalline forms of solid phosphoric acid catalyst.

Kieselguhr clay and phosphoric acid have a $P_2O_5$ content of 82 percent or greater were combined at a weight ratio of 1 to 2 at a temperature of 170° C. This material was extruded with an extruder through a die to produce extrudates approximately 5 mm diameter. Only amorphous character was detected by X-ray with the green extrudates. The extrudates thus produced where then used in the crystallization experiments described in the following Examples II to VIII. The crystallinity of the finished catalysts was determined by X-ray diffraction. The method employed used standard X-ray diffraction techniques using NBS alpha-alumina as a reference material (see the specifications for the exact test method). Therefore, the crystallinity values of orthophosphate and pyrophosphate reported in the following examples are not absolute crystallinity values but are instead relative to alpha-alumina.

EXAMPLE II

A batch of amorphous solid phosphoric acid green extrudates from Example I was subjected to a crystallization process in a small oven in batches of 100 to 150 grams. The oven contained a means of allowing once through air and steam to be added at a controlled rate as well as a means for closely controlling the oven temperature. After about 20 minutes under 3 percent steam level at an oven temperature of 250° C., the catalyst was removed and analyzed for its crystallinity. Only crystalline silicon orthophosphate was detected with an X-ray intensity of 10.7 percent relative to an alpha-alumina standard. No crystalline silicon pyrophosphates were detected.

EXAMPLE III

A batch of amorphous solid phosphoric acid green extrudates from Example I was subjected to a crystallization process in the same small oven as in Example II. After about 20 minutes under 22 percent steam level at 250° C. oven temperature, the catalyst was removed and analyzed for its crystallinity. Only crystalline form of silicon orthophosphate was detected with a relative X-ray intensity of 6.4 percent relative to an alpha-alumina standard. The results of this example and the results of Example II indicate that steam has no effect on the production of crystalline silicon pyrophosphates at temperatures below 250° C.

EXAMPLE IV

A batch of amorphous solid phosphoric acid green extrudates from Example I was subjected to a crystallization process in the same small oven as in Example II. After about 50 minutes under 3 percent steam level at 392° C. oven temperature, the catalyst was removed and analyzed for its crystallinity. Only crystalline form of silicon orthophosphate was detected with a relative X-ray intensity of 44.9 percent relative to an alpha-alumina standard.

EXAMPLE V

A portion of the crystalline solid phosphoric acid catalyst from Example IV was subjected to a reconditioning process in the same small oven as in Example II for an additional 20 minutes at 392° C. under 26 percent steam. This additional treatment reduced the total silicon phosphate X-ray intensity to 41.7 percent relative to the alpha-alumina standard with the relative intensity ratio between silicon orthophosphate and silicon pyrophosphate of 7.1. This example shows that both steam and a temperature are critical factors in producing a solid phosphoric acid catalyst having crystallites of ortho and pyrophosphates.

EXAMPLE VI

A batch of amorphous solid phosphoric acid green extrudates from Example I was subjected to a crystallization process in the same small oven as in Example II. After about 50 minutes in an 18 percent steam atmosphere at 392° C. oven temperature, the catalyst was removed and analyzed for its crystallinity. Crystallites of both silicon orthophosphate and silicon pyrophosphate were detected with a total X-ray intensity of 40 percent relative to an alpha-alumina standard. The relative intensity ratio between the silicon orthophosphate and silicon pyrophosphate was 17.2. This result indicates that a high steam rate at temperatures above 250° C. promotes the formation of crystalline silicon pyrophosphate in a crystalline solid phosphoric acid catalyst.

EXAMPLE VII

A portion of the crystalline solid phosphoric acid catalyst from Example VI was subjected to a reconditioning process in the same small oven as in Example II for an additional 20 minutes at 392° C. in a 3 percent steam atmosphere. This additional treatment reduced the total silicon phosphate X-ray intensity to 38.0 percent relative to the alpha-alumina standard while the relative intensity ratio between silicon orthophosphate and silicon pyrophosphate dropped to 12.7

EXAMPLE VIII

A batch of amorphous solid phosphoric acid green extrudates from Example I was subjected to a crystallization process in the same small oven as in Example II. After about 70 minutes in a 27 percent steam atmosphere at 430° C. oven temperature, the catalyst was removed and analyzed for its crystallinity. Crystalline form of both silicon orthophosphate and silicon pyrophosphate were detected with a total X-ray intensity of 47.7 percent relative to an alpha-alumina standard. The relative intensity ratio between the silicon orthophosphate and silicon pyrophosphate was 12.3.

EXAMPLE IX

A number of solid phosphoric acid catalysts prepared essentially as set forth in Example I and finished at various calcination conditions were analyzed for relative silicon orthophosphate and silicon pyrophosphate X-ray intensity. The results of this analysis can be found in Table 1 below.

The analyzed catalysts were then tested for catalyst life by placing the catalysts in an olefin polymerization process plant. The test was conducted at a pressure of about 68.0 atmospheres, with propylene feed, at a liquid hourly space velocity of from 1.8–2.1, and at a temperature of from 149° to 230° C. The catalyst life was determined as gallons of polymer product produced per pound of catalyst.

TABLE 1

Solid Phosphoric Acid Catalyst Test Results

| Catalyst | Relative Total X-ray Intensity | Silicon Orthophosphate to Silicon Pyrophosphate Relative Intensity Ratio | Relative Catalyst Life |
|---|---|---|---|
| 1 | 37.4 | 10.1 | 1.00 |
| 2 | 38.5 | 19.0 | 1.47 |
| 3 | 40.1 | 31.9 | 1.21 |
| 4 | 41.4 | 10.3 | 1.76 |
| 5 | 42.2 | 11.5 | 1.59 |
| 6 | 41.4 | 16.3 | 1.65 |
| 7 | 44.5 | 152.4 | 1.62 |
| 8 | 44.5 | 9.2 | 1.68 |
| 9 | 45.5 | 83.3 | 1.91 |
| 10 | 45.0 | 3.5 | 1.97 |
| 11 | 45.4 | 18.2 | 1.97 |
| 12 | 45.2 | 2.7 | 2.00 |
| 13 | 46.8 | 5.9 | 1.94 |
| 14 | 46.9 | 60.6 | 2.09 |
| 15 | 45.7 | 40.2 | 2.21 |

A comparison of the total crystallinity values of Table 1, that is the Relative Total X-ray Intensity Values, to the catalyst life values demonstrates that total crystallinity is directly related to catalyst stability. The greater the total silicon phosphate relative X-ray intensity of the solid phosphoric acid catalyst, the more stable the solid phosphoric acid catalyst will be during the olefin polymerization processes as measured by the catalyst life.

EXAMPLE X

Green extrudates were prepared in the manner described in Example I. That is, kieselguhhr and phosphoric acid with a $P_2O_5$ content of 82 percent were combined at a weight ratio of 1 to 2 and a temperature of 170° C. The green extrudates were then dried in a muffle furnace at 288° C. (550° F.) for 60 hours. In this manner, a prior art catalyst was prepared which conformed to the teachings of U.S. Pat. No. 2,116,151. The sample was analyzed by powder x-ray diffraction using a National Bureau of Standards alpha-alumina reference material and the technique which is described in detail in the instant specification. The prior art catalyst showed 32% total silicon phosphate crystallite x-ray intensity relative to alpha-alumina. The silicon orthophosphate to silicon pyrophosphate ratio was 0.13, which indicated that 4% silicon orthophosphate crystallite x-ray intensity and 28% silicon pyrophosphate crystallite x-ray intensity were present. This prior art catalyst was therefore distinguishable from the instant invention.

EXAMPLE XI

Green extrudates prepared as in Example I above were dried in a muffle furnace at 288° C. (550° F.) for thirty minutes and then further calcined at 480° C. (900° F.) for 16 hours. In this manner, a prior art catalyst was prepared which conformed to the teachings of U.S. Pat. No. 2,275,1892. At this point, the sample was analyzed by x-ray powder diffraction and a value of 40% total silicon phosphate crystallite intensity was observed. A silicon orthophosphate to silicon pyrophosphate ratio of 0.7 was determined, which indicated that 17% silicon orthophosphate crystallite x-ray intensity and 23% silicon pyrophosphate crystallite x-ray intensity were present.

The sample was further subjected to steam calcination at 260° C. with 6 mol % steam in air for 16 hours followed by 300° C. (500° F.) calcination for 15 minutes in dry air. The sample was again analyzed by x-ray powder diffraction and 41% total silicon phosphate crystallite x-ray intensity was detected. The silicon orthophosphate to silicon pyrophosphate ratio was 0.69, which indicates that 17% silicon orthophosphate x-ray intensity and 24% silicon pyrophosphate x-ray intensity were present. Therefore, a method of manufacture representative of the prior art did not produce catalyst of the instant invention.

EXAMPLE XII 35 grams of diatomite were mixed with 15 grams of $P_2O_5$ to form a dry mixture. The mixture was combined with 27.9 grams of 85% orthophosphoric acid to form a coarse dough which was then dried in an oven at 95° C. Finally, the catalyst was steamed for 2 hours at 400° C. (725° F.). The prior art catalyst prepared was in accordance with the teachings of U.S. Pat. No. 3,661,801. A sample was analyzed by powder x-ray diffraction and found to possess 15% total silicon phosphate crystallite x-ray intensity relative to alpha-alumina. The silicon orthophosphate to silicon pyrophosphate ratio was 3.6, which indicated that 13% silicon orthophosphate crystallite x-ray intensity and 3% silicon pyrophosphate crystallite intensity were present. The sample did not meet the specifications for catalyst of the instant invention.

EXAMPLE XIII 50 grams of diatomite silica agglomerated particles were soaked in 70 wt. % orthophosphoric acid for about 30 minutes. After the excess solution was drained away, the catalyst was dried in an oven at 95° and then calcined with 6 mol % steam at 400 degree C. (750° F.) for 2.5 hours. U.S. Pat. No. 2,960,477 discloses this procedure. At this point a sample was analyzed by x-ray powder diffraction and 16% total silicon phosphate crystallite x-ray intensity was measured. The silicon orthophosphate to silicon pyrophosphate ratio was determined to be 3.1, which indicated that 12% silicon orthophosphate crystallite x-ray intensity and 4% silicon pyrophosphate crystallite x-ray intensity were present.

The catalyst was then soaked with a 1.5 pH solution consisting of 0.76 st. % $H_2SO_4$ for 10 minutes. The catalyst was separated from the $H_2SO_4$ solution by filtration and the catalyst was washed with water and dried in an oven at 95° C. The dry catalyst was an with 50 wt. % orthophosphoric acid solution for 1.5 hours and dried again at 95 degree C. to remove substantially all free water. Then the catalyst was subjected to 3 hours of drying at 200° C. A sample was analyzed by powder x-ray diffraction and a value of 4% total silicon phosphate crystallinity x-ray intensity relative to alpha-alumina was observed. The silicon orthophosphate to silicon pyrophosphate ratio was 3.9, which indicated that 3% silicon orthophosphate crystallite x-ray intensity and 1% silicon pyrophosphate crystallite x-ray intensity were present. Neither sample qualified as a catalyst of the instant invention.

What is claimed is:

1. A process for conversion of hydrocarbons or oxygenated hydrocarbons in the presence of a solid phosphoric acid catalyst by contacting at hydrocarbon conversion conditions a hydrocarbon or oxygenated hydrocarbon feedstock with a solid phosphoric acid catalyst having a total silicon phosphate x-ray intensity greater than 40 percent relative to alpha-alumina and comprising silicon pyrophosphate crystallites with at least 1.0 percent x-ray intensity and silicon orthophosphate crystallites with at least 30 percent x-ray intensity, both relative to alpha-alumina, with the desired phosphoric acid catalyst crystallinity produced by crystallizing an amorphous mixture of an acid oxide of phosphorus and a siliceous material in a crystallizing means where the crystallizing means is operated at a temperature of from 350° to 450° C., and at a steam concentration of from 10 to 50 mole percent based upon the total vapor in the crystallizing means.

2. The process of claim 1 further characterized in that the amorphous mixture of phosphorus oxide and a siliceous material is crystallized in the presence of from 10 to 25 mole percent steam based upon the total vapor in the crystallizing means.

3. The process of claim 1 further characterized in that the catalyst is crystallized for a total period of time ranging from 20 to 120 minutes or more.

4. A process for conversion of hydrocarbons or oxygenated hydrocarbons in the presence of a solid phosphoric acid catalyst by contacting at hydrocarbon conversion conditions a hydrocarbon or oxygenated hydrocarbon feedstock with a solid phosphoric acid catalyst having a total silicon phosphate x-ray intensity greater than 40 percent relative to alpha-alumina and comprising silicon pyrophosphate crystallites with at least 1.0 x-ray intensity and silicon orthophosphate crystallites with at least 30 percent x-ray intensity, both relative to alpha-alumina with the desired phosphoric acid catalyst crystallinity produced by crystallizing an amorphous mixture of an acid oxide of phosphorus and a siliceous material in a crystallizing means comprising a crystallization zone which operates at a temperature of from 350° to 450° C. and contains from 10 to 25 mole percent steam based upon the total vapor in the crystallizing zone and for a total time period ranging from 20 to 120 minutes or more.

5. The process of claim 4 further characterized in that the siliceous material component of the solid phosphoric acid catalyst is selected from the group consisting of kieselguhr clay, diatomaceous earth, and artificially prepared porous silica.

6. The process of claim 4 further characterized in that the weight ratio of phosphorus oxide to siliceous material of the amorphous mixture ranges from 1 to 10.

7. The process of claim 4 further characterized in that the catalyst is crystallized in a single zone crystallizing means.

8. The process of claim 4 further characterized in that the acid oxide of phosphorus is a polyphosphoric acid.

9. The process of claim 4 further characterized in that the process for conversion of hydrocarbons is alkylation of an aromatic hydrocarbon with an olefin-acting agent and in that the contacting of the hydrocarbon or oxygenated hydrocarbon feedstock with the solid phosphoric acid catalyst occurs at conditions including a temperature of from 100° to 390° C., a pressure of from 1 to 130 atmospheres, and a liquid hourly space velocity of from 0.5 to 50 $hr^{-1}$.

10. The process of claim 4 further characterized in that the process for conversion of hydrocarbons is catalytic condensation and in that the contacting of the hydrocarbon or oxygenated hydrocarbon feedstock with the solid phosphoric acid catalyst occurs at conditions including a temperature of from 140° to 290° C. and a pressure of from 6.8 to 102 atmospheres.

11. The process of claim 4 further characterized in that the process for conversion of hydrocarbons is hydration of an olefinic hydrocarbon and in that the contacting of the hydrocarbon or oxygenated hydrocarbon feedstock with the solid phosphoric acid catalyst occurs at conditions including a temperature of from 250° C. to about 350° C., a pressure from 34 to 340 atmospheres.

* * * * *